(12) United States Patent
Potkay et al.

(10) Patent No.: US 12,233,189 B2
(45) Date of Patent: Feb. 25, 2025

(54) SMART ARTIFICIAL LUNG AND PERFUSION SYSTEMS

(71) Applicant: THE REGENTS OF THE UNIVERSITY OF MICHIGAN, Ann Arbor, MI (US)

(72) Inventors: Joseph Potkay, Plymouth, MI (US); Robert H. Bartlett, Ann Arbor, MI (US); Alvaro Rojas-Pena, Ann Arbor, MI (US)

(73) Assignees: The Regents of The University of Michigan, Ann Arbor, MI (US); United States Government As Represented by the Department of Veterans Affairs, Washington, DC (US)

( * ) Notice: Subject to any disclaimer, the term of this patent is extended or adjusted under 35 U.S.C. 154(b) by 1101 days.

(21) Appl. No.: 17/054,909

(22) PCT Filed: Jun. 18, 2019

(86) PCT No.: PCT/US2019/037675
§ 371 (c)(1),
(2) Date: Nov. 12, 2020

(87) PCT Pub. No.: WO2019/246057
PCT Pub. Date: Dec. 26, 2019

(65) Prior Publication Data
US 2021/0228792 A1    Jul. 29, 2021

Related U.S. Application Data

(60) Provisional application No. 62/687,456, filed on Jun. 20, 2018.

(51) Int. Cl.
*A61M 1/16* (2006.01)
*A61M 1/36* (2006.01)

(52) U.S. Cl.
CPC ........ *A61M 1/1698* (2013.01); *A61M 1/1603* (2014.02); *A61M 1/3638* (2014.02);
(Continued)

(58) Field of Classification Search
CPC .............. A61M 1/1698; A61M 1/1603; A61M 1/3638; A61M 2205/3327;
(Continued)

(56) References Cited

U.S. PATENT DOCUMENTS

2005/0025680 A1    2/2005    Monzyk et al.
2011/0129389 A1    6/2011    Brady et al.
(Continued)

FOREIGN PATENT DOCUMENTS

JP    H08182758 A    7/1996
KR    10-2014-0073353 A    6/2014
(Continued)

OTHER PUBLICATIONS

David M. Hoganson et al., Paracorporeal lung assist devices as a bridge to recovery or lung transplantation in neonates and young children, vol. 147, Issue 1, 2014, pp. 420-427.

International Search Report and Written Opinion of the International Searching Authority issued in PCT/US2019/037675, mailed Oct. 15, 2019; ISA/US.

*Primary Examiner* — Leslie R Deak
(74) *Attorney, Agent, or Firm* — Harness, Dickey & Pierce, P.L.C.

(57) ABSTRACT

An artificial lung system for a patient having a membrane lung system having an gas inlet, a blood inlet, a blood outlet, and an exhaust; a gas system operably coupled to the gas inlet of the membrane lung system; a gas phase $CO_2$ sensor disposed downstream of the exhaust of the membrane lung system and monitoring an exhaust gas $CO_2$ ($EGCO_2$) level and/or an blood oxygen saturation sensor disposed upstream of the blood inlet of the membrane lung system and monitoring a blood oxygen saturation level; and a feedback
(Continued)

controller receiving the $CO_2$ signal and/or blood oxygen saturation signal and outputting a control signal to control gas flow and/or blood flow.

8 Claims, 12 Drawing Sheets

(52) U.S. Cl.
CPC ............ *A61M 2205/3327* (2013.01); *A61M 2205/3334* (2013.01); *A61M 2230/202* (2013.01); *A61M 2230/205* (2013.01)

(58) Field of Classification Search
CPC .... A61M 2205/3334; A61M 2230/202; A61M 2230/205
See application file for complete search history.

(56) References Cited

U.S. PATENT DOCUMENTS

| | | | |
|---|---|---|---|
| 2015/0034082 A1* | 2/2015 | Kimm | A61M 16/0051 128/202.16 |
| 2016/0015881 A1 | 1/2016 | Utsugida et al. | |
| 2017/0021080 A1* | 1/2017 | Bonczar | A61G 12/008 |
| 2017/0258980 A1 | 9/2017 | Katsuki et al. | |

FOREIGN PATENT DOCUMENTS

| | | | | |
|---|---|---|---|---|
| WO | 2011021978 A1 | 2/2011 | | |
| WO | WO-2019246320 A1 * | 12/2019 | ......... | A61B 5/14542 |

* cited by examiner

Fig-2C

SMART ARTIFICIAL LUNG AND PERFUSION SYSTEMS

CROSS-REFERENCE TO RELATED APPLICATIONS

This application is a 371 U.S. National Phase of International Application No. PCT/US2019/037675, filed Jun. 18, 2019 which claims the benefit of U.S. Provisional Application No. 62/687,456, filed on Jun. 20, 2018. The entire disclosures of the above applications are incorporated herein by reference.

GOVERNMENT SUPPORT

This invention was made with the government support under Grant Nos. HD015434 and HL140995, awarded by the National Institutes of Health. The Government has certain rights in the invention.

FIELD

The present disclosure relates to a smart artificial lung and perfusion systems and, more particularly, relates to a smart controller system for use with artificial lung systems and overall systems thereof.

BACKGROUND AND SUMMARY

This section provides background information related to the present disclosure which is not necessarily prior art. This section provides a general summary of the disclosure, and is not a comprehensive disclosure of its full scope or all of its features.

For more than two decades, there has been a growing awareness of the potential for ventilator-induced injury, showing that deliberate use of low tidal volumes decreased mortality. It was also shown that the most prevalent in requiring mechanical ventilation are those patients with Chronic Obstructive Pulmonary Disease (COPD). The present teachings provide smart controllers that use a negative feedback control loop(s) for artificial lungs and perfusion systems.

Specifically, an estimated 16 million Americans are affected with some degree of Chronic Obstructive Pulmonary Disease (COPD), accounting for 150,000 deaths per year. There has been a widespread success in single or double lung transplantation in the 1990s. However, the disparity between the number of patients that need lung transplants and the availability of lungs to be transplanted means demands has steadily outgrown the supply and can result in substantial delays while awaiting transplantation. The current methods for supporting patients with lung disease are not generally adequate, efficient, or sufficiently cost effective to act as a bridge to transplantation.

The notion of a lung-assisted device was first raised in 1967 by Rashkind et al., who proposed a pumpless oxygenator for temporary lung help in cystic fibrosis, ARDS, and congenital heart disease. Over the past decade, critical medicine has made tremendous contributions to improve outcomes in patients suffering from acute lung injury. Unfortunately, no current artificial lung system can respond to the changing needs of the patient.

Generally, mechanical ventilation provides some relief, but can damage the lungs through barotrauma, volutrauma, and biotrauma. Mechanical ventilation is a rescue therapy, applied to patients who require long-term support due to inefficiency in breathing parameters. Mechanical ventilators can be pressure based or flow based controlled. It is usually the decision of the clinician to set an optimal value for the ventilator manipulated variable.

Similarly, artificial lung systems can provide respiratory support without the drawback of ventilator-induced injury. These systems can provide rest for the lung allowing it to heal or serve as a bridge to transplantation. Artificial lungs have been developed as complete artificial organs, and results of many investigations based on innovative concepts have been reported. In fact, in Japan, artificial lungs have been used in clinical treatments and are expected to be the next generation treatment for severe respiratory failure. In open-heart surgery, artificial lungs are used for extracorporeal circulation to maintain gas exchange, and the commercial products currently available perform fairly well. However, patients with severe respiratory/circulatory failure have required long-term assist with extracorporeal membrane oxygenation (ECMO). The number of artificial lungs used for ECMO has shown significant growth in recent years. However, ECMO is very labor intensive, complex, time-limited, costly, and prone to infection.

Again, as mentioned herein, no current artificial lung system can respond to the changing needs of the patient. Conventional systems thus risk removing too much $CO_2$ during periods of rest or improved lung function (causing hypocapnia and blood alkalosis) or not enough $CO_2$ during activity or poor lung function (causing dyspnea and discomfort). Thus, activity, comfort, and rehabilitation are severely limited using current conventional systems.

Therefore, according to the principles of the present teachings, an automated controller for artificial lungs that varies $CO_2$ clearance to meet a patient's changing metabolic needs is provided. In some embodiments, the controller can control blood flow servoregulation to automate oxygen delivery. To validate the present teachings, a prototype, benchtop, laptop-based controller was developed that modulates pump-driven airflow through an artificial lung based on exhaust gas $CO_2$ content and was further validated its operation in in vitro and in vivo studies.

Furthermore, according to the principles of the present teachings, automatic control strategies and systems for artificial lungs are provided that simultaneously control the partial pressures of blood oxygen and carbon dioxide in patients with severe lung diseases.

Still further, according to the principles of the present teachings, the smart artificial lung controller system can respond to changes in $CO_2$ and oxygenation that is necessary for patients with end-stage lung diseases. The present principles can be integrated with artificial lungs and other wearable lungs assisted devices. Accordingly, the smart artificial lung controller and system can improve patient outcome and optimize the perfusion parameters. Moreover, the smart artificial lung controller system can improve patient safety by fast control reference tracking and good disturbance rejection under varying conditions.

Still further, accordingly to the principles of the present teachings, the present technology-development improves patient rehabilitation from lung disease by engineering the first artificial lung systems that automatically respond to the changing needs of the patient.

According to the principles of the present teachings, smart controllers are developed for artificial lung systems for the treatment of human patients as well as for the organ and limb perfusion systems. In some embodiments, the smart controller uses a negative feedback control loop to precisely control perfusion parameters to not only automate these systems, but would also provide real-time optimization of perfusion parameters leading to improved outcomes. These benefits are achieved through a combination of electrical hardware, sensors, firmware, and software design.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2C is a servoregulator user interface.

Corresponding reference numerals indicate corresponding parts throughout the several views of the drawings.

DETAILED DESCRIPTION

Figure 1A:
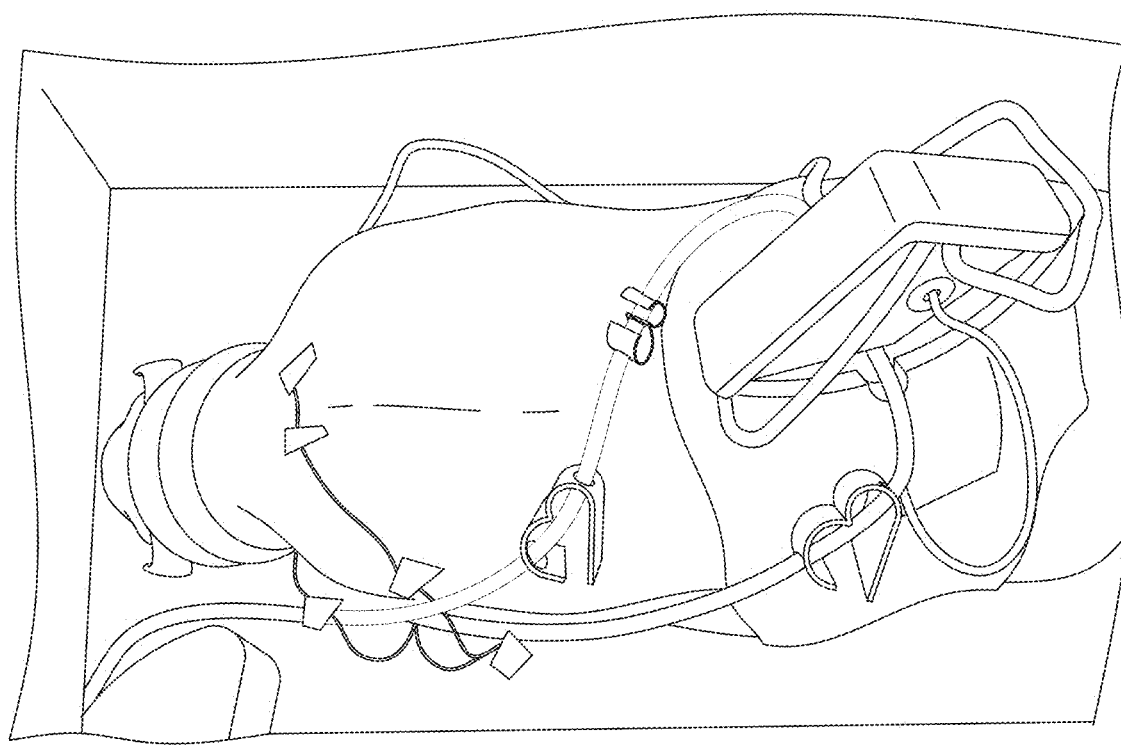
FIG. 1A illustrates a sheep with AV shunt and Novalung IIa. Hypercapnia was induced by decreasing minute ventilation (MV).

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Up to 24 million Americans are living with chronic lung disease; it is the third leading cause of death in the United States and is responsible for more than 150,000 deaths each year. Acute respiratory distress syndrome (ARDS) has a mortality rate between 30 and 50% and affects 200,000 Americans each year. As patients progress to end stage lung disease (ESLD), their health progressively worsens despite optimal care, medication, and supplemental oxygen. They become increasingly disabled, wheel chair then bed ridden, and the dyspnea becomes so severe that patients cannot complete a sentence or swallow liquids. Mechanical ventilation alleviates some of the symptoms, but the high airway pressures and oxygen concentrations can result in varotrauma, volutrauma, and biotrauma, and can exacerbate the original illness, possibly resulting in multi-organ failure. Lung transplantation is an option with excellent outcomes, but the waiting list is long and many patients are not candidates due to age or other comorbidities.

Artificial lung (AL) technologies have been developed to provide respiratory support without the drawback of ventilator-induced injury. In acute cases, ALs are used to provide respiratory support, thereby enabling the lung to heal while the patient rehabilitates. In chronic cases, ALs have served as a bridge to transplant, increasing survival, and improving quality of life. Recent experience has shown that AL-based $CO_2$ removal promptly relieves all symptoms of ELSD, can improve oxygenation and decrease pulmonary hypertension, and allows rehabilitation. To increase patient mobility and thus improve the ability to exercise and rehabilitate, ambulatory extracorporeal membrane oxygenation (ECMO) systems have been developed in which the AL, blood pump, computer, battery, and oxygen cylinder are mounted to a wheeled pole. These systems enable limited exercise and improve rehabilitation, but are limited to ICU use. Companies and researches are developing wearable AL systems to retain the rehabilitation advantages of ambulatory ECMO, but provide the patient with improved mobility and potentially the ability to return home.

While these traditional, ambulatory, and wearable AL systems can and will increase patient quality of life through improved mobility and rehabilitation, none of them can automatically adjust to the changing needs of the patient. Specifically, none can automatically adjust $CO_2$ removal or oxygenation in response to changes in either disease status or patient activity. Exacerbation of chronic obstructive pulmonary disease (COPD), one of the etiologies of ESLD, is one example of change in disease status. COPD exacerbations are a major cause of increased morbidity, mortality, and poor health status, and place a considerable burden on our health care system. During acute exacerbations of COPD, patient $PaCO_2$ can increase from normal or slightly elevated levels (40-50 mmHg) to between 60 and even up to 130 mmHg and blood pH can decrease from 7.4 to 7.1 or lower. Approximately 15% of COPD patients per year have exacerbations requiring hospital admission; between 10% and 25% of patients admitted with hypercapnic ($pCO_2$>50 mm Hg) respiratory failure due to COPD die in the hospital. Reduced exacerbation frequency is therefore an important therapeutic target.

During exercise in ESLD patients, $CO_2$ tension typically increases by 25 mmHg and much more in some patients, resulting in extreme discomfort and dyspnea. All current AL systems thus risk either not removing enough $CO_2$ during periods of increased metabolic rate, activity, or during an exacerbation of their disease (resulting in dyspnea and increased minute ventilation) or removing too much $CO_2$ during periods of decreased metabolism, rest, or a return of lung function (resulting in hypocapnia and blood alkalosis). Further, although the main need for most ESLD patients is $CO_2$ removal, a subset of patients also requires supplemental blood oxygenation. As with $CO_2$ removal, the patient's need for oxygen varies with metabolism and activity. A large drop in oxygen level risks tissue hypoxia in patients, increasing the probability of multi-organ failure and increasing mortality. It is thus critical that AL systems be able to respond rapidly and quickly to the changing needs of the patient.

For patients already on AL support in the ICU, hospital staff need to manually adjust AL sweep flow (to adjust $CO_2$ clearance) or blood flow (to adjust oxygenation) or any change in patient activity, metabolism, or disease status as monitored by patient blood $CO_2$ ($PaCO_2$) and $O_2$ ($SvO_2$) levels. Further, changes inpatient blood $CO_2$ or $O_2$ may not be immediately detected and adjustments to sweep or blood flow may not be immediate or precise. There is thus significant room to improve the comfort and quality of life for these patients, as wells as decrease staff monitoring and intervention. For wearable AL systems that may allow the patient to return home, the ability to automatically adjust sweep and blood flow will be critical for patient health and daily activity. Overall, AL systems that automatically adjust to the changing metabolic needs of the patient would thus represent a huge increase in the quality of life of ESLD patients, by allowing a wide range of metabolic activity (including exercise and rehabilitation in ICU and at home settings) and changes in disease status. The development of a controller to achieve this goal in traditional, ambulatory, and wearable AL systems is an object of the present teachings.

It is anticipated that the principles of the present teachings will first be used in clinical applications to augment existing ECMO and ambulatory ECMO systems to provide automated control of $CO_2$ removal by membrane lungs in the ICU. Such a system allows automated control of the AL sweep as to respond to the patient's moment-to-moment changing $CO_2$ clearance needs. Such a system reduces burden on hospital staff, improves patient comfort (through tighter control of blood $PaCO_2$), and enables improved activity and rehabilitation. These principles and associated $CO_2$ control are further validated in acute and chronic animal studies as discussed herein.

Figure 1B:
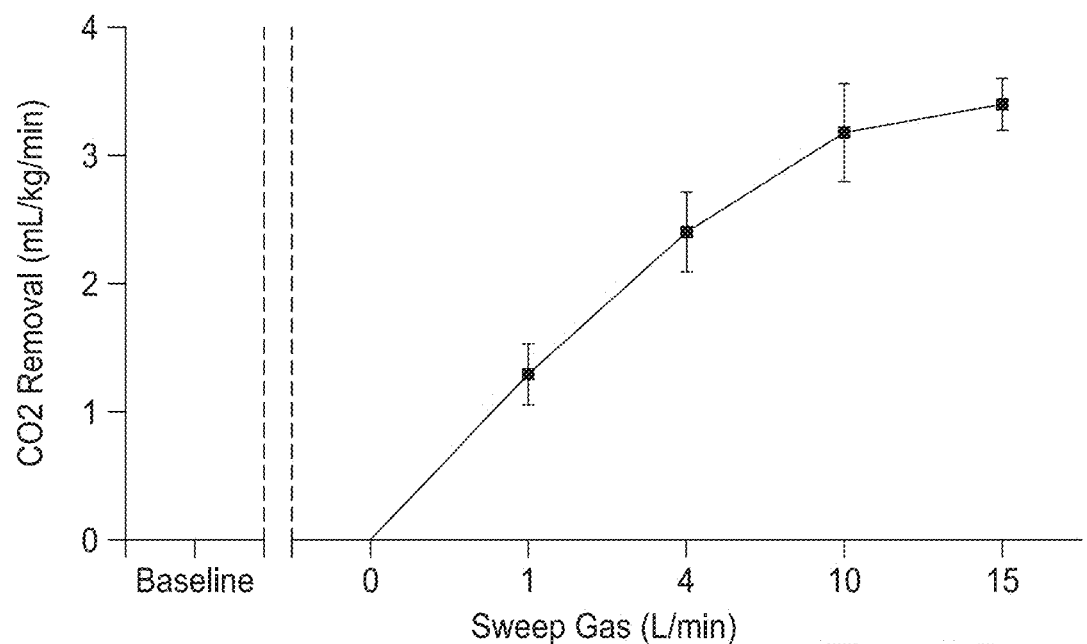
FIG. 1B is a diagram where AL sweep flow increased to a max of 2.4±0.4 mL/kg/min.
Figure 1C:
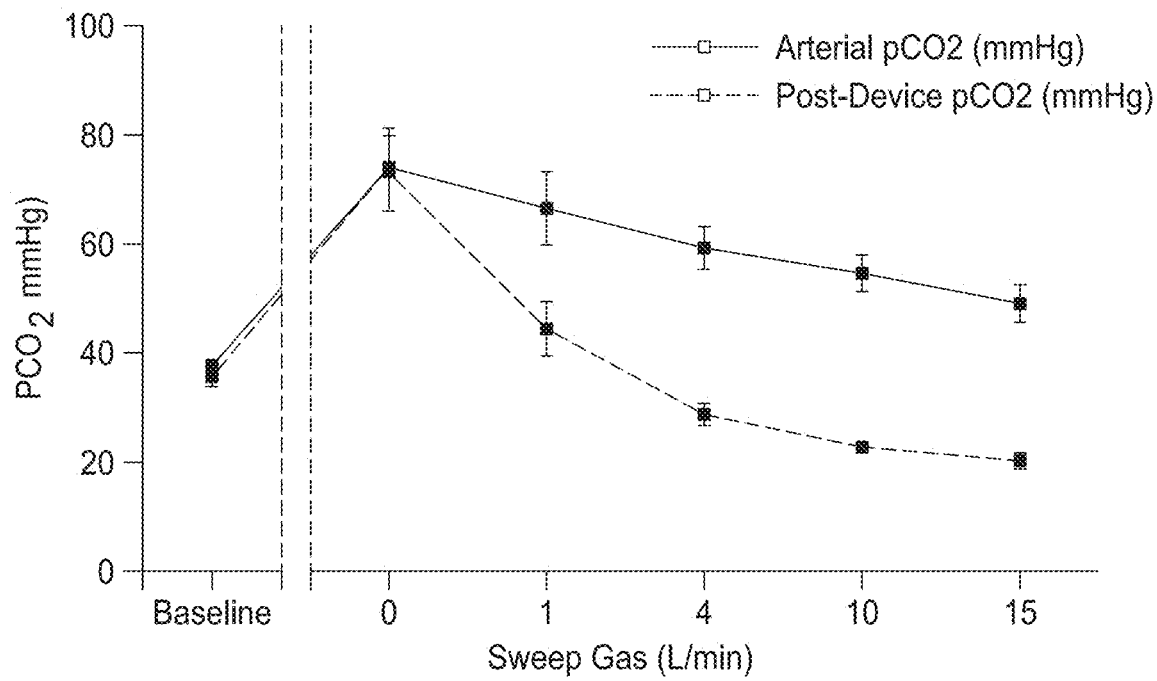
FIG. 1C is a where Baseline $PaCO_2$ increased from 37±3 mmHG to 74±15 mmHg after MV was decreased, then decreased as sweep gas flow was increased, reaching 49±7 mmHg at 15 L/min sweep flow.

Various acute and chronic extracorporeal ovine models have been developed since 1974, including recent models for research on ESLD. Animal data for $CO_2$ removal via subclavian vessels is shown in FIG. 1A-1C. After recovery from anesthesia, a low-resistance membrane oxygenator (Novalung iLA) was attached in an AV configuration for up to 37 hours. Hemodynamics remained stable with average AL flows of 1.3±0.14 L/min without affecting cardiac output. Device function was evaluated in each animal (61±6 kg) while awake and spontaneously breathing (data not shown) and while mechanically ventilated with hypercapnia induced, as shown in FIG. 1A-1C. This preliminary data demonstrates a varying sweep flow can drastically affect $CO_2$ removal, as shown in FIG. 1B, and sweep flows up to 15 L/min can significantly reduce respiratory rate (RR) and decrease arterial $PaCO_2$ (74 to 49 mmHg) using a blood flows of ~1 L/min, as shown in FIG. 1C.

Figure 2A:
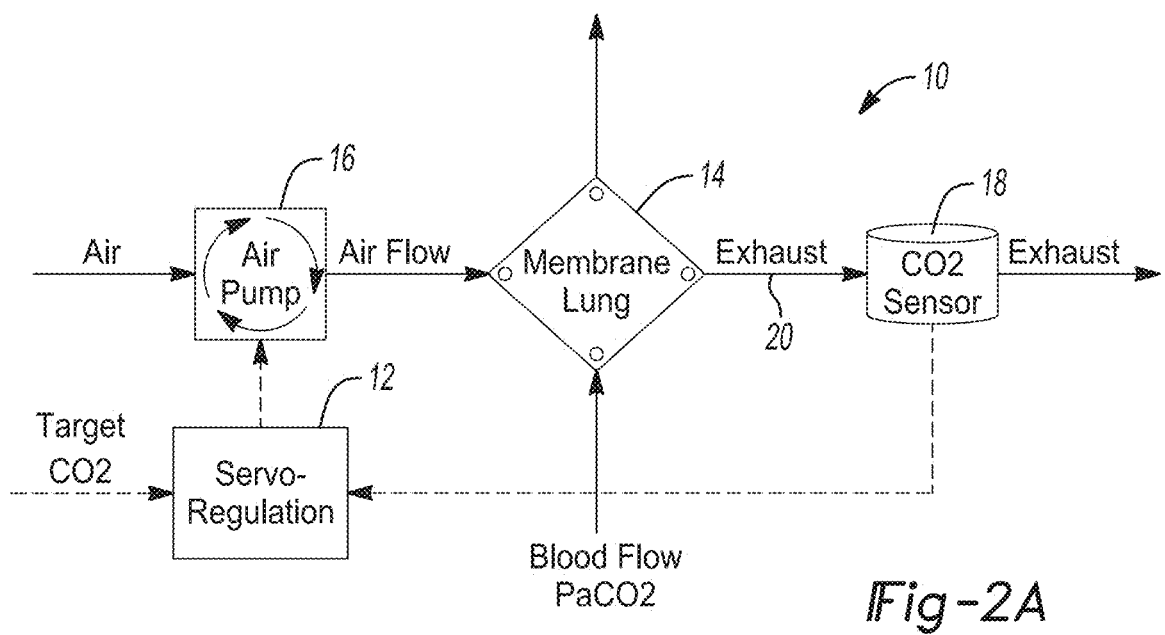
FIG. 2A is an in vitro testing configuration.
Figure 2B:
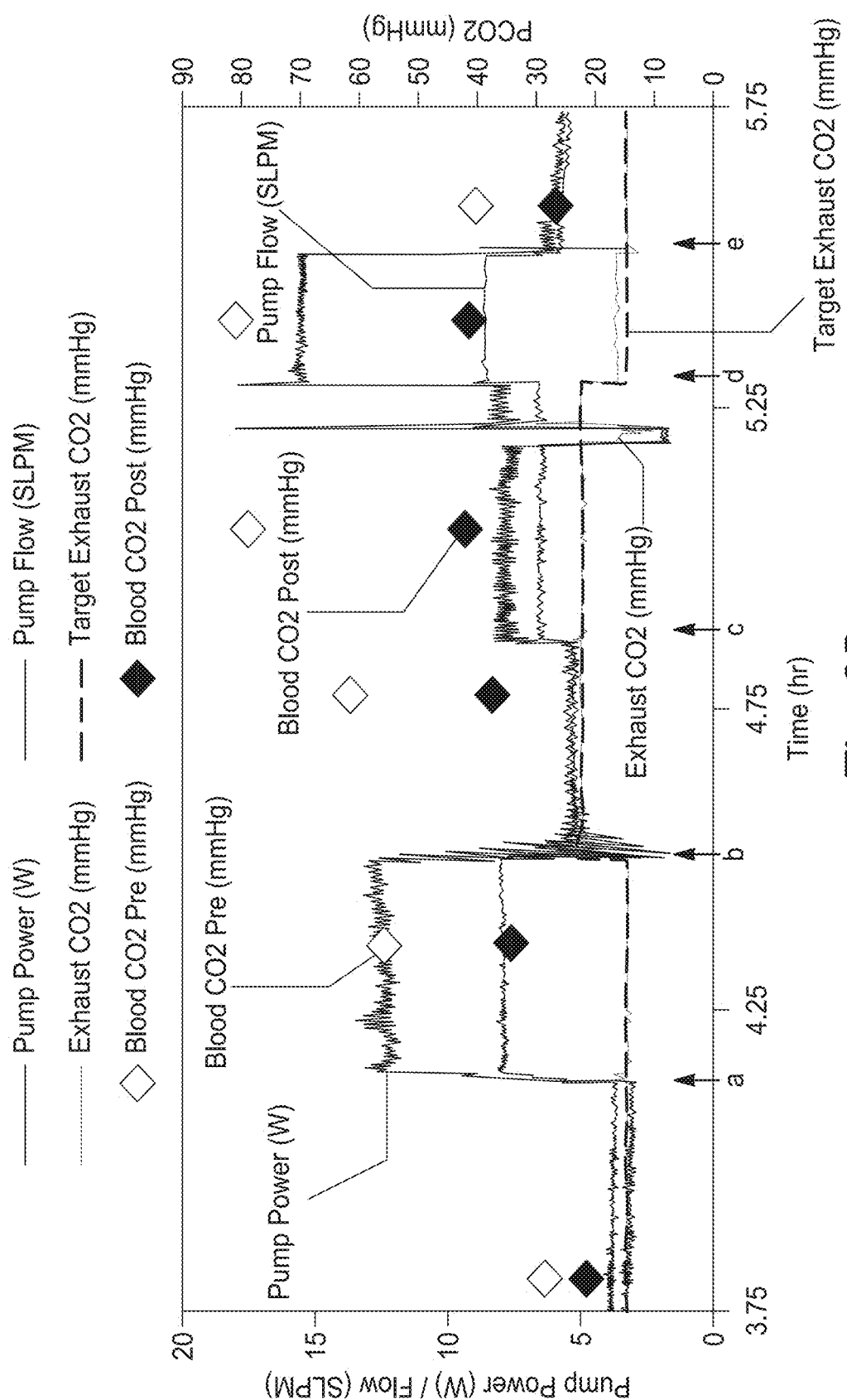
FIG. 2B is a subset of measured servoregulation data.
Figure 2C:
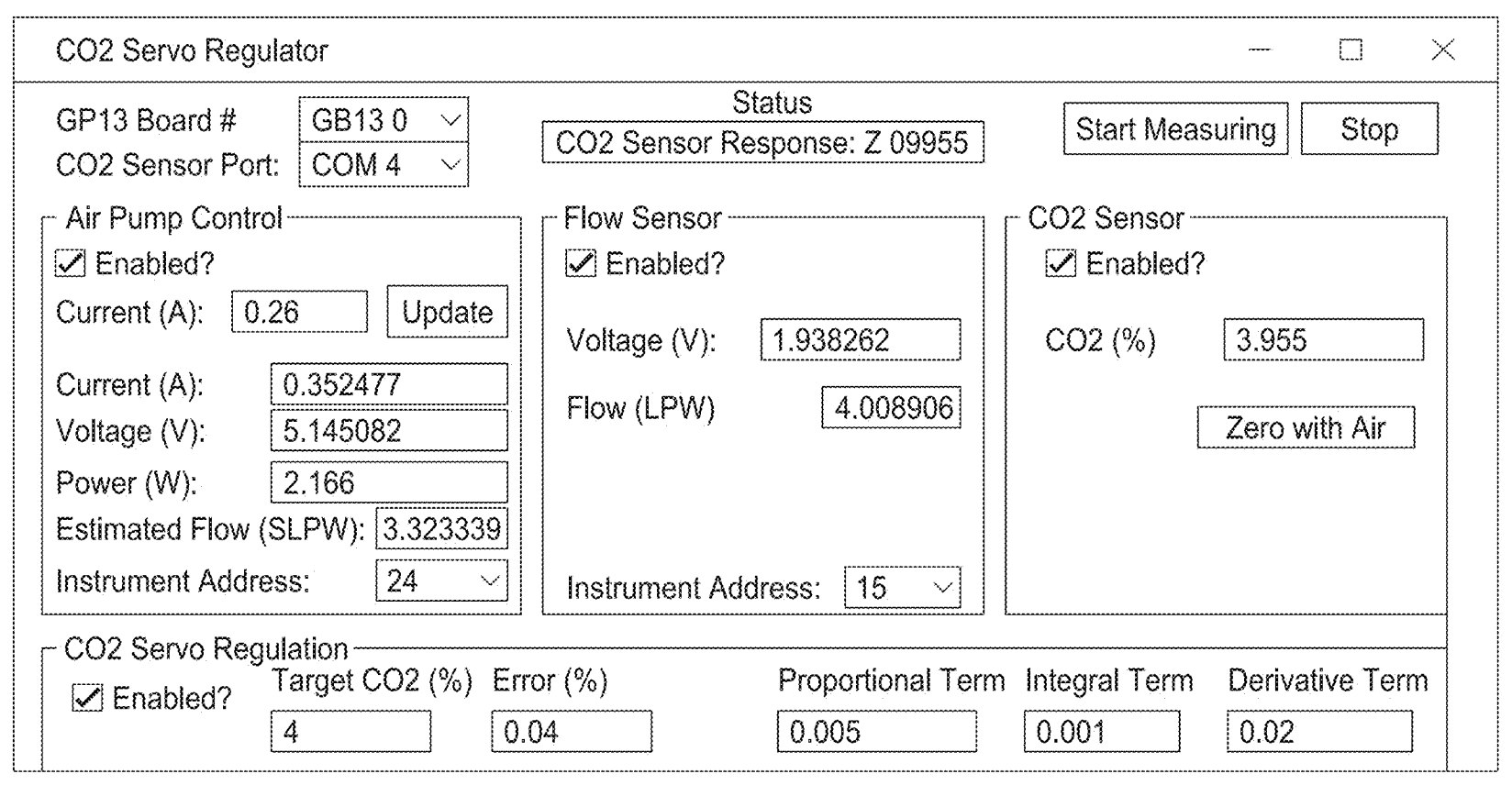

According to the principles of the present teachings, a prototype laptop-driven, benchtop system that implements the functionality of the present $CO_2$ servoregulation control system 10 is shown in FIGS. 2A-2C. The $CO_2$ servoregulation control system 10 uses a proportional-integral-derivative (PID) feedback controller 12 to modulate pump-driven sweep flow through an smart artificial lung and perfusion system 14 to achieve a desired exhaust gas $CO_2$ ($EGCO_2$) level. If $EGCO_2$ content increases (e.g. due to increased patient activity), the servoregulation controller 12 increases sweep flow to remove more $CO_2$. In contrast, if $EGCO_2$ decreases, the sweep flow automatically and rapidly decreases to reduce $CO_2$ removal as required. The graphical user interface and servoregulation controller were programmed using Microsoft Visual Studio on a laptop computer. The air pump 16 (10 k hour KNF N86 brushless DC gas pump) was controlled through a programmable power source (Keithley 2400) via an IEEE-488 instrument interface (Keithley KUSB-488B). Communication with $CO_2$ sensor 18 ($CO_2$ Meter GC-0017; 0-20%) was achieved via a USB RS232 serial interface. In order to mitigate the effect of exhaust gas condensate on $CO_2$ sensor functionality, the AL exhaust gas 20 was directed through a desiccant (calcium chloride) and then a water trap before being passed on to the $CO_2$ sensor 18. The servoregulation controller 12 was tested over a period of 6 hours using a Medtronic Minimax Plus oxygenator and anticoagulated bovine blood. Changes in patient activity were simulated by varying inlet blood $pCO_2$, as shown in FIG. 2B. Target exhaust $CO_2$ content was varied to challenge the PID. The PID automatically adjusted the sweep flow to rapidly (<1 min in most cases) achieve the desired $EGCO_2$ level in all tests. All inlet blood $pCO_2$ levels (30-80 mmHg; measured by blood draws) were converted to outlet blood $pCO_2$ between 23-38 mmHG. Condensate was trapped/absorbed and did not affect the function of the $CO_2$ sensor 18 during the testing period.

Figure 3A:
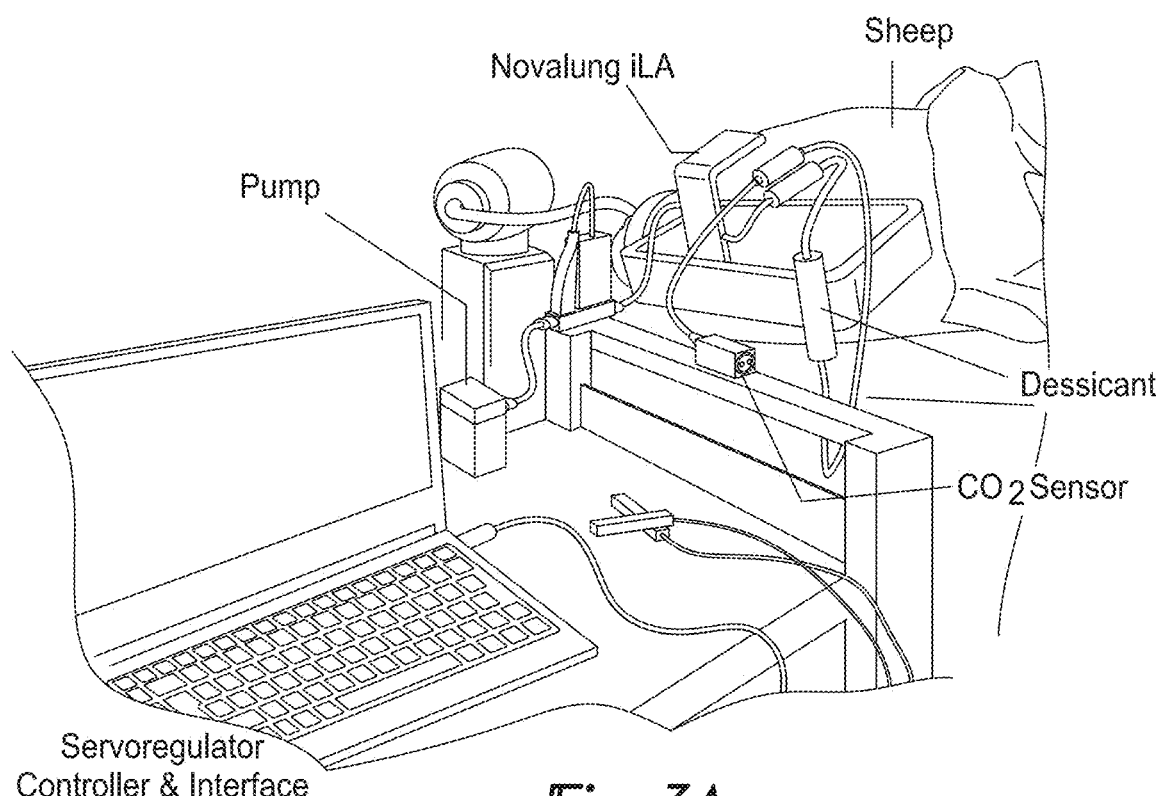
FIG. 3 is an in vivo testing of the laptop-based $CO_2$ servoregulation system.
Figure 3B:
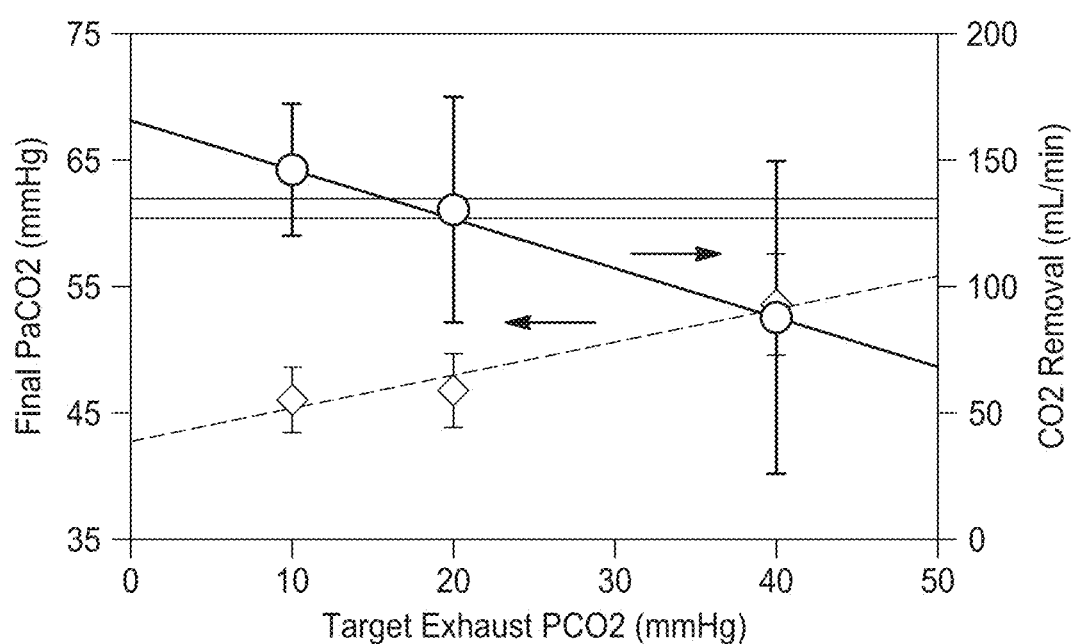

The laptop-based sweep gas servoregulation controller 12 was then tested in sheep to investigate the effect on animal physiology. Three healthy sheep (60±5 kg) were placed under general anesthesia and connected to an AV AL (Novalung iLA) via the subclavian vessels. Health and hypercapnia conditions were induced by setting minute ventilation (MV) to 100% or 50% of baseline resulting $PaCO_2$ of 40-45 mmHg (100% MV) or 53-72 mmHg (50% MV). Blood flow through the Novalung was either 0.5 or 1 L/min (10-20% of cardiac output). After a baseline $PaCO_2$ stabilized, the sweep gas servoregulation controller 12 was then turned on with a target $EGCO_2$ of either 10, 20, or 40 mmHg and the animal was allowed to stabilize (~15 minutes) and final steady state $PaCO_2$ was recorded, as shown in FIGS. 3A and 3B. As in in vitro studies, the servoregulation controller 12 rapidly (<1 minute) responded to achieve the target $EGCO_2$.

Figure 4A:
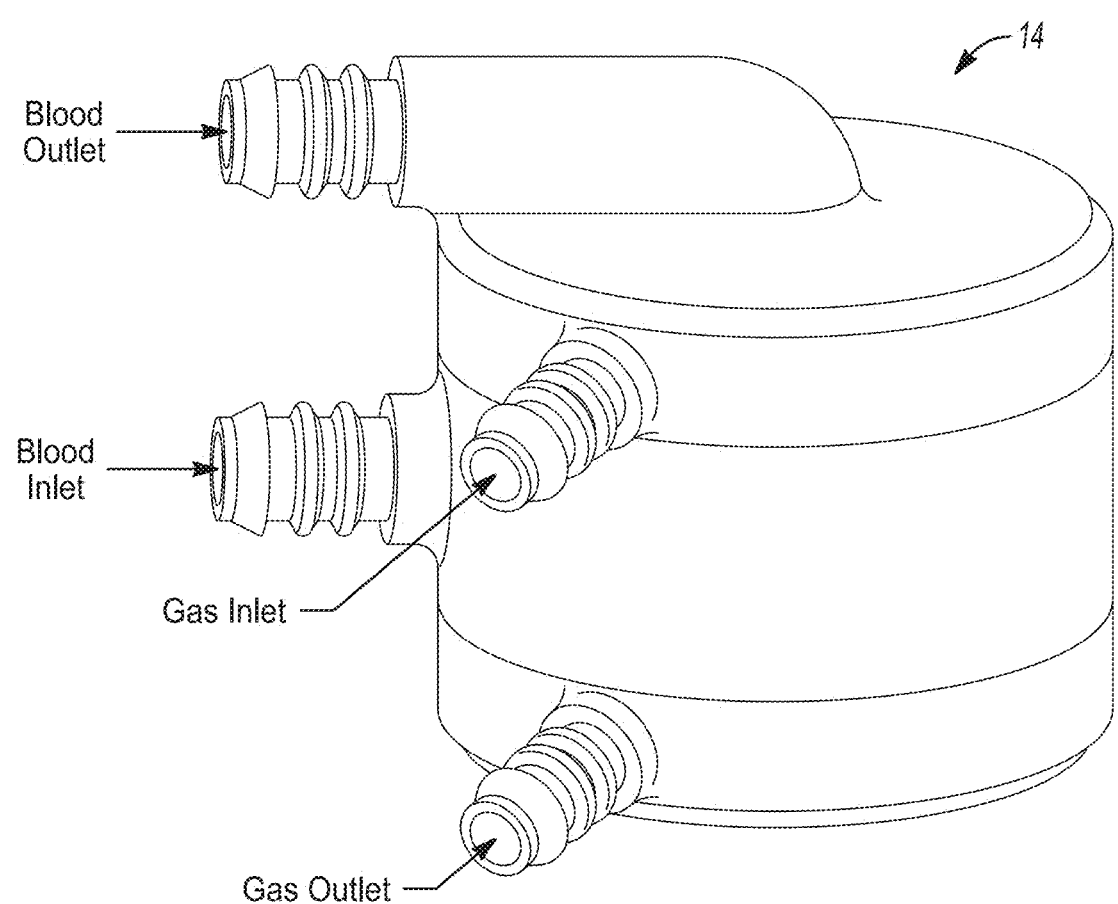
FIG. 4A is a photo of the smart artificial lung and perfusion system.
Figure 4B:
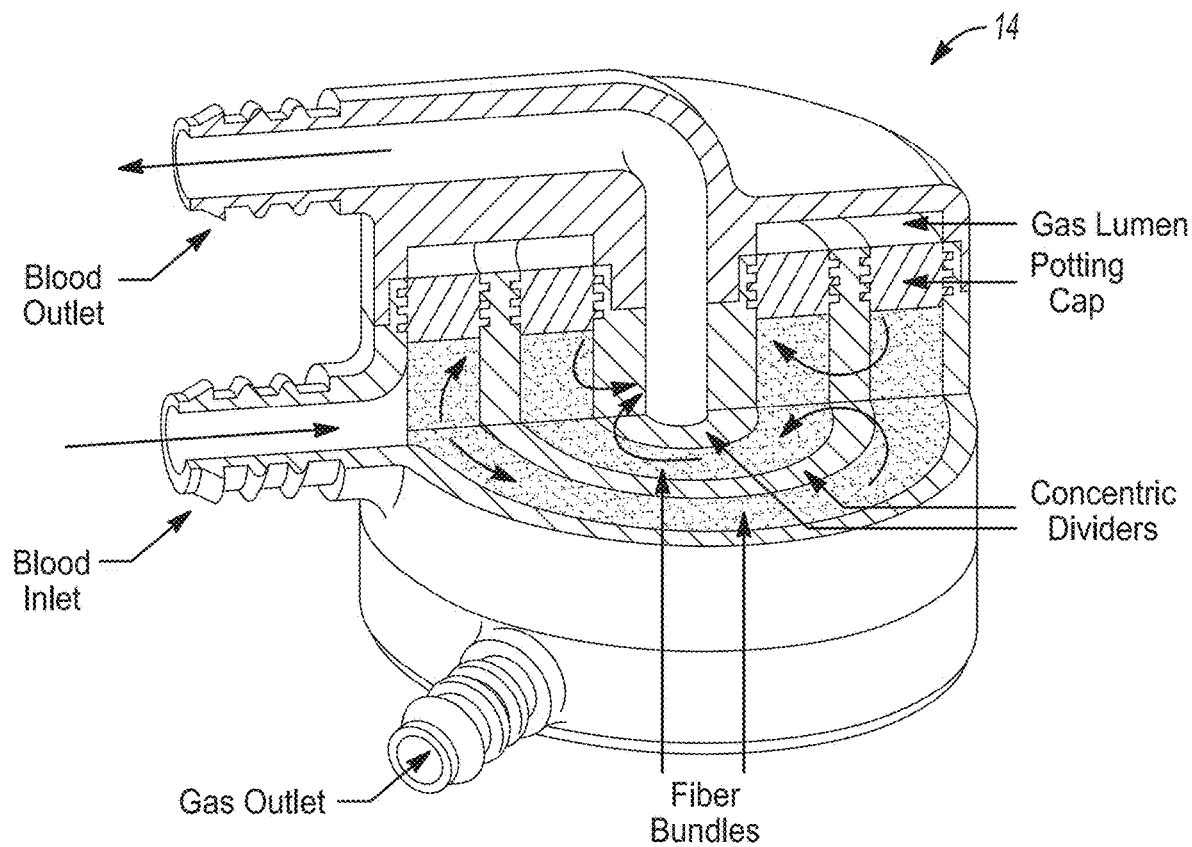
FIG. 4B is a sectional view of the smart artificial lung and perfusion system.
Figure 4B:
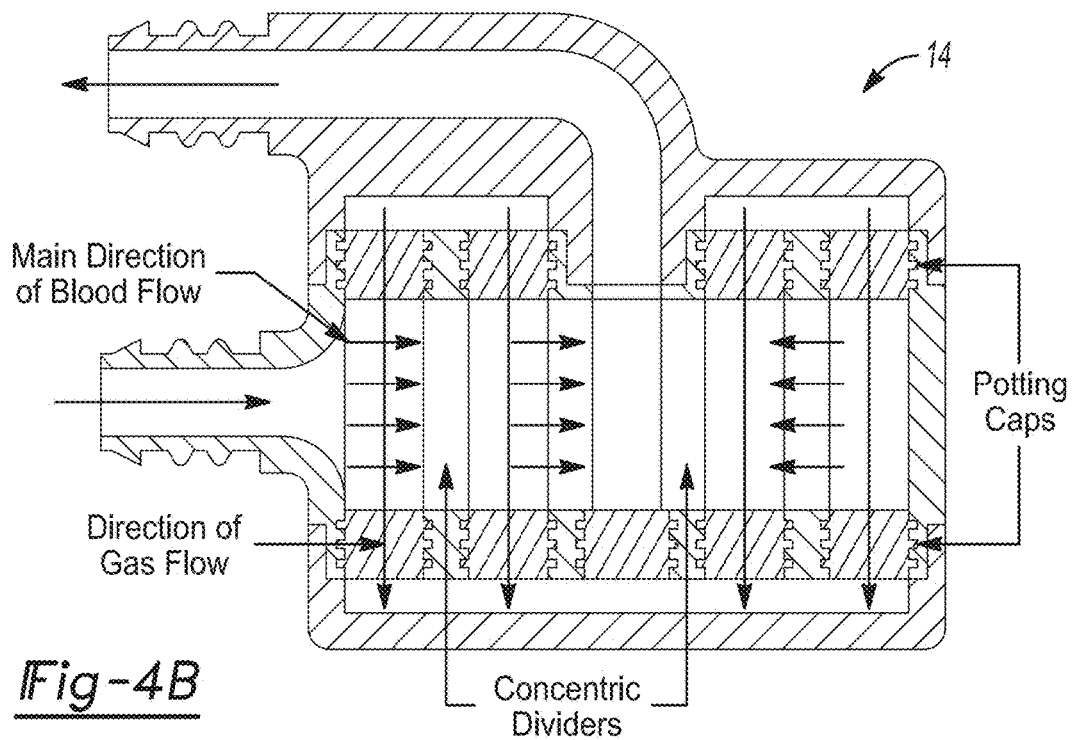
Figure 4C:
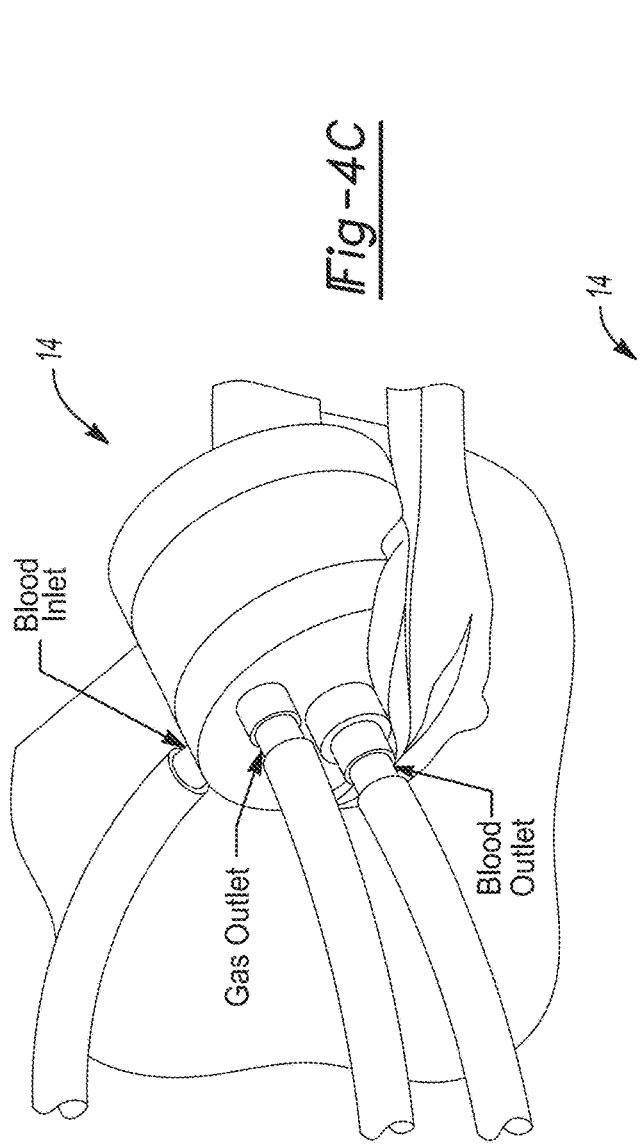
FIG. 4C is a picture of the smart artificial lung and perfusion system prototype during in vivo testing.
Figure 4D:
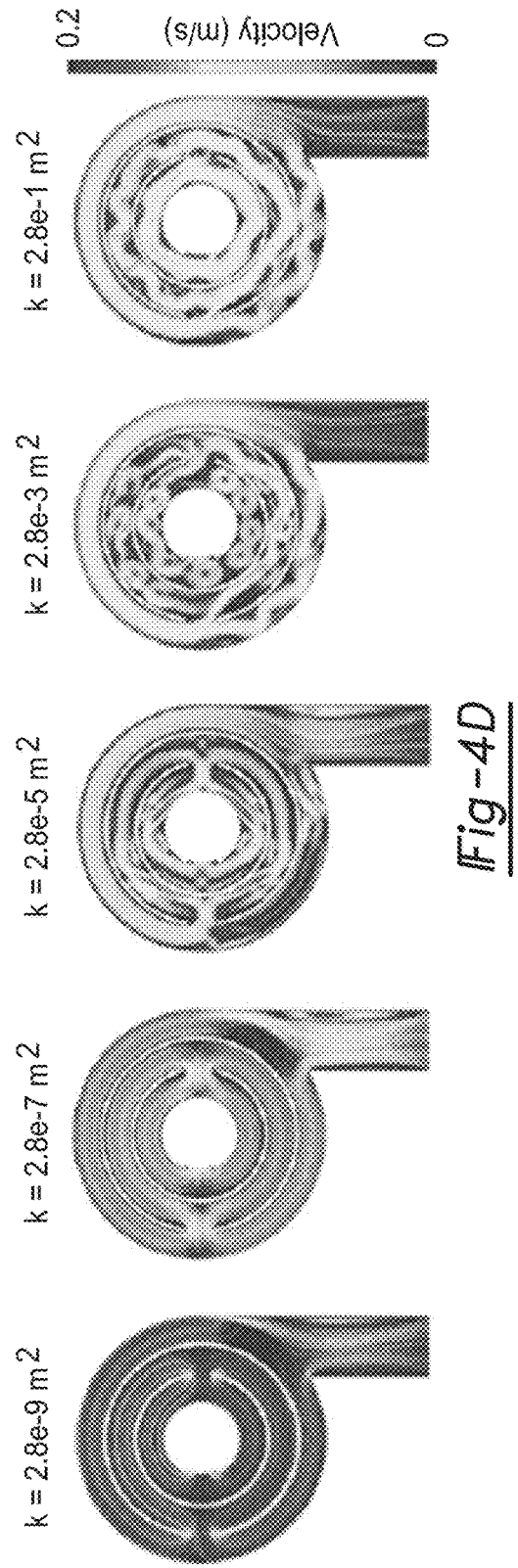
FIG. 4D is a CFD velocity profiles across the smart artificial lung and perfusion system.
Figure 5:
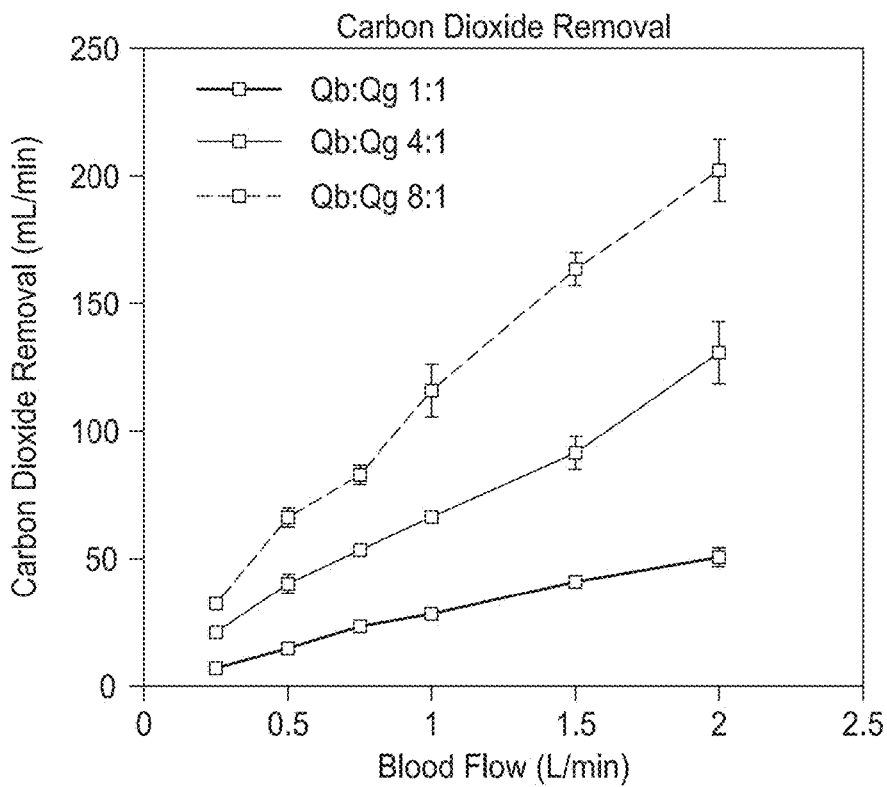
FIG. 5 is in vitro $CO_2$ removal of smart artificial lung and perfusion system.
Figure 7:
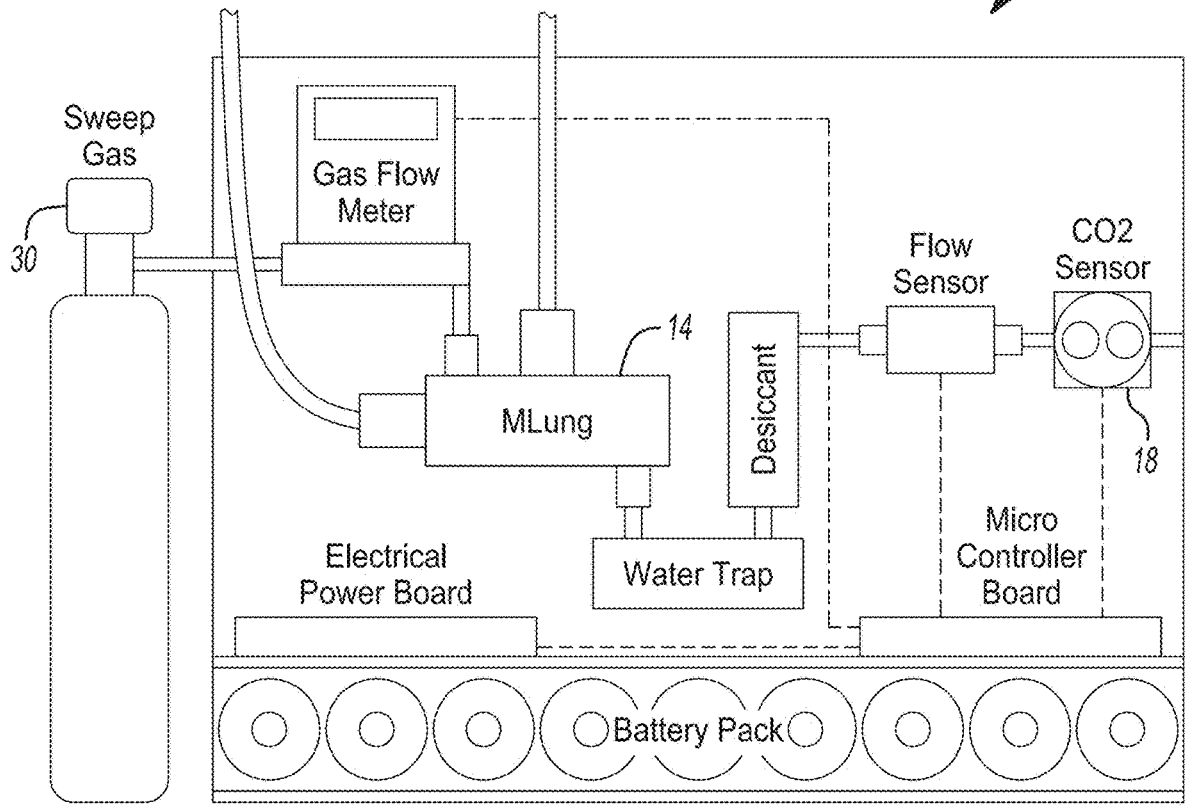
FIG. 7 is a 12×12×4" physical layout of the servoregulation control system.

According to the principles of the present teachings, a new smart artificial lung and perfusion system 14 is provided that has been optimized for $CO_2$ removal in adult ESLD, as shown in FIGS. 4A-4D. The smart artificial lung and perfusion system 14 employs a unique gated concentric design, as shown in FIGS. 4A-4C, which creates secondary flow mixing that allows for high blood flow per unit surface area thereby minimizing stagnant flow, transit time, and thrombosis. The smart artificial lung and perfusion system 14 uses a polymethyl pentene (PMP) fibers and a short (2 cm) gas flow path, thereby maintaining a large gas concentration gradient and minimizing water condensation in the exhaust sweep gas. The device was developed using computational fluid dynamical (CFD) and flow visualization, as shown in FIG. 4D. Prototypes of the membrane lung were fabricated using polyurethane casting (providing extremely smooth blood contacting surfaces) and stereolithography. The 0.28 $m^2$ fiber bundle has porosity of 0.63 as determined using CFD, for use with subclavian artery pressure to achieve a 1 L/min flow with a cardiac output of 5 L/min. In vitro $CO_2$ exchange of the smart artificial lung and perfusion system 14 with 1-2 L/min blood flow is 120-200 mL/min, as shown in FIG. 5. Its rated flow is 2 L/min. Pressure drop at 1 L/min is 45 mmHg. This gas exchange performance was validated in acute in vivo experiments in anesthetized sheep (data not shown). The smart artificial lung and perfusion system 14 achieves similar $CO_2$ removal as the Novalung iLA while using much less fiber surface area (0.28 vs 1.3 $m^2$).

According to these teachings, $CO_2$ servoregulation control system 10 is thus provided for membrane lungs that adjusts $CO_2$ clearance by a membrane lung to automatically respond to the changing metabolic needs of the patient and is suitable for integration into nearly all existing and future AL systems.

The pathophysiology of ESLD patients is increased alveolar dead space resulting in $CO_2$ retention, respiratory acidosis, moderate hypoxemia, and eventual pulmonary hypertension. Any activity causes an increase in metabolic rate that increases $CO_2$ production. Any exacerbation of the disease will decrease $CO_2$ clearance by the lungs. In both cases, symptoms of the disease will be intensified. AL systems can provide respiratory support, but no current systems can automatically adjust to the changing metabolic needs of the patient, thereby significantly limiting patient activity and moment-to-moment comfort. According to the present teachings, a servoregulation controller 12 that automatically adjusts $CO_2$ clearance (by adjusting sweep gas flow supplied by gas cylinders) to meet the needs of the patient is provided. As discussed, increasing sweep gas flow can dramatically increase $CO_2$ clearance. Further, all metabolically-produced $CO_2$ can be removed using a blood flow of only 20% of cardiac output. These teachings are demonstrated in a laptop-driven, benchtop servoregulator that modulated pump-driven air sweep gas flow based on exhaust gas $CO_2$ content.

Similar to the system above, the servoregulation controller 12 in this aim will automatically modulate sweep gas flow to vary $CO_2$ clearance as required by the patient. With a method in place to modulate $CO_2$ clearance (via sweep gas flow rate), a means to measure metabolic activity is required, or more specifically a means to measure patient $PaCO_2$. Since a long-term blood $pCO_2$ sensor does not exist, the $CO_2$ content in the exhaust gas 20 of the smart artificial lung and perfusion system 14 is used as a surrogate marker of patient metabolic activity. In our in vitro and in vivo preliminary studies, exhaust gas $pCO_2$ appears to be an adequate measure of patient metabolic activity. Our prototype servoregulator successfully used exhaust $pCO_2$ to modulate sweep flow as required to increase or decrease $CO_2$ clearance in both benchtop and animal tests based on changing $PaCO_2$ levels.

Our preliminary studies focused on a pump-driven sweep (air) flow that would be suitable for a wearable AV $CO_2$ removal system. In this embodiment, the $CO_2$ servoregulation control system 10 is redesigned to use sweep gas supplied by gas cylinders and controlled via mass flow controllers. Further, the $CO_2$ servoregulation control system 10 is designed to be fully integrated, compact, and battery driven and is implemented using FDA mandated design controls. Such a system is broadly applicable to nearly all current AL systems, including ECMO, ambulatory ECMO and most wearable ALs under development.

The specifications for our $CO_2$-based servoregulator system for ALs are 1). Applicable in veno-venous (VV), veno-arterial (VA), or AV configurations (with minor adjustments) and with virtually any membrane lung for maximum applicability; 2) size and weight should be compatible with an ambulatory or wearable system; 3) ability to adjust sweep gas flow between 1 and 16 L/min to vary $CO_2$ clearance; 4) servoregulation of the sweep gas based on exhaust gas $CO_2$ content; 5) battery driven operation with time between recharge >48 hours; 6) easy replacement of all components, with an algorithm for assessment and replacement; 7) monitors sweep gas flow and exhaust gas $CO_2$ and calculates $CO_2$ removal; and 8) developed using FDA mandated design controls and validation and verification procedures.

Figure 6:
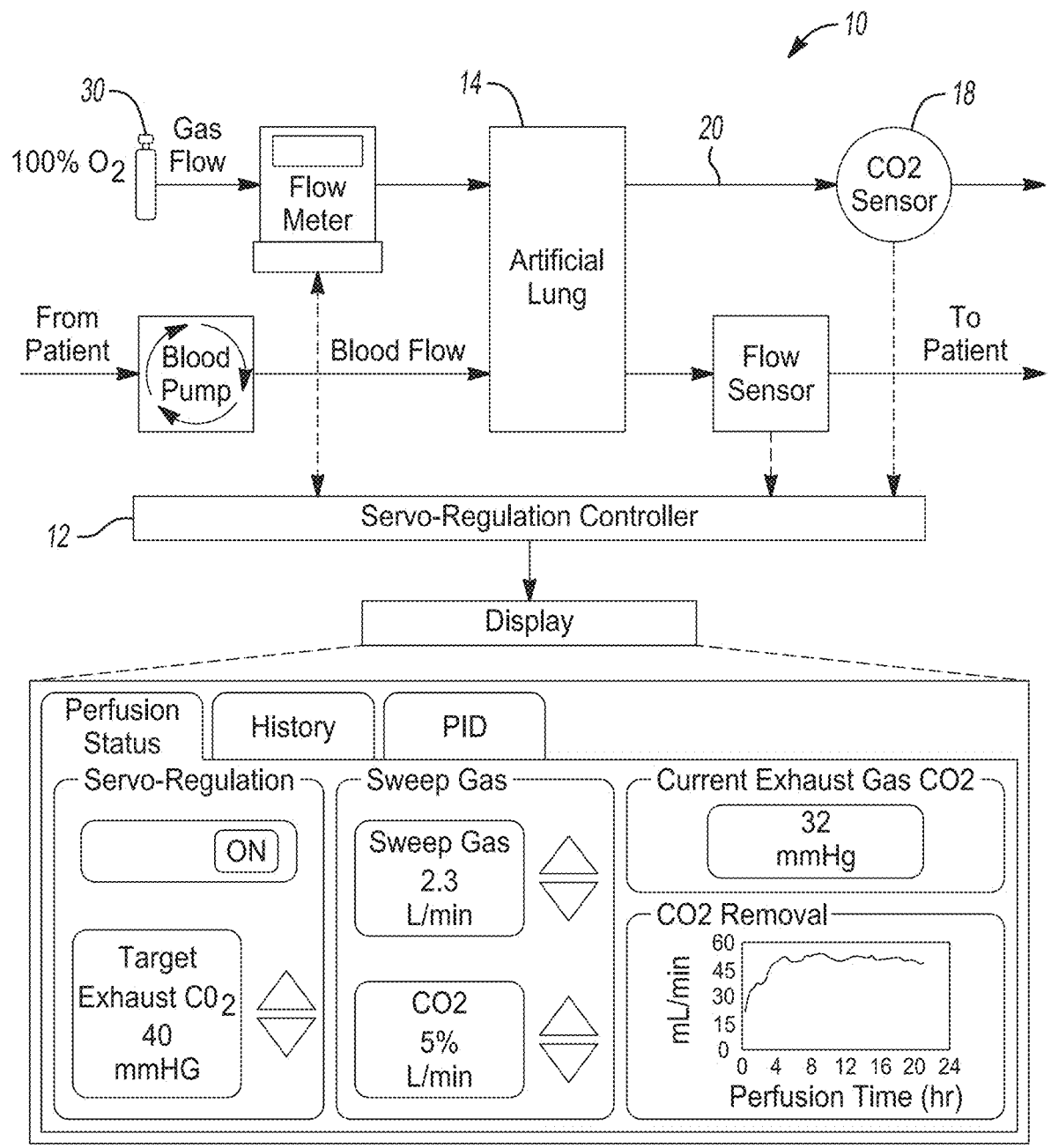
FIG. 6 is a system block diagram for the $CO_2$-based sweep for servoregulation system and concept drawing of the graphical user interface.

A system level diagram of the initial implementation of the sweep gas servoregulation system 10 is shown in FIG. 6. This system differs from preliminary studies in several ways: 1) sweep gas is supplied by gas cylinders 30 and controlled via a mass flow controller 32; 2) the $CO_2$ servoregulation control system 10 is compatible with battery-driven operation; 3) all components is integrated into a small, lightweight enclosure for use in bedside (ICU), ambulatory, or wearable AL systems; and, 4) care is taken to ensure safety and quality assurance. All components are specified, designed, documented, and tested with an eventual FDA submission in mind.

The heart of the servoregulation system 10 is the servoregulation controller 12, as shown in FIG. 6. The servoregulation controller 12 communicates with and directs the actions of each component in the system 10. It auto-regulates sweep gas flow to alter $CO_2$ removal based on exhaust gas $CO_2$ content. In order to minimize size and weight of the system, all individual components are integrated into the system 10 at the board (i.e. printed circuit board) level when possible. A diagram of the planned enclosure for all components is shown in FIG. 6.

The system display shown in FIG. 6 will show all relevant parameters (gas flow, exhaust $CO_2$ content, $CO_2$ clearance, etc.), both their current value and their value over time. Air flow (Sensirion SFM4100; 0-20 L/min) and $CO_2$ sensors ($CO_2$ Meter GC-0017; 0-150 mmHg) measure $CO_2$ clearance. As in preliminary studies, a water trap and desiccant are used to prevent condensate for reaching the $CO_2$ sensor 18. Battery charging, conversion of wall AC power to DC, and conversion of battery voltage to a stable supply voltage for system components will all be achieved using commercially-available integrated circuits (e.g. Linear Technology LTC4079 battery charging IC; Maxim MAX5087A linear voltage regulator).

All components of the control system 10 are specified, designed, and documented according to FDA mandated design controls. Requirements for each component are traced through implementation and testing to connect design output to design input. A full risk and fault tree analysis of the system and components are performed through a full design review and mitigation policies are implemented. All software is designed according to IEC $6_2304$ for critical medical device software. A microcontroller specifically designed for safety critical systems (Texas Instruments Hercules TMS570) is used as the central controller. Static analysis and coverage analysis are performed on all software to reduce coding errors. As in preliminary studies, servoregulation is implemented using a software-based proportional integral derivative PID feedback controller. Initial PID tuning is achieved using the Ziegler-Nichols method. The physical enclosure is constructed form machined acrylic for initial in vitro testing. Once proven, the enclosure is fabricated using polyurethane casting for use in the in vivo tests.

The servoregulation control system 10 will have warning signals that are activated when the following are detected: 1) low air flow indicating air pump failure or disconnected tubing; 2) low battery; or 3) high humidity in exhaust gas line after desiccant, thereby indicating imminent failure of the desiccant. In some embodiments, the controller will integrate a moisture/liquid sensor in the housing to monitor for water trap or blood leaks.

Testing of all individual components and the integrated system will initially be accomplished with our bench system and water flow. The system was perfused with water at room temperature continuously for 5 days. The sweep gas is 5% $CO_2$ in air, allowing evaluation of the exhaust gas $CO_2$ sensor under continuous use. This bench testing will verify the operation of the battery pack, control electronics, sensors, display, and warnings for a range of flow rates, conditions, and battery charge percentages. After verification of the durability of components, bench testing will proceed with fresh bovine blood. The bench test system includes a second blood reservoir and a large oxygenator to create variable blood gas composition, thereby mimicking patient activity. A blood pump supplies blood to the large oxygenator and the sweep gas is supplied with a $CO_2$ concentration of 3-13. Since the blood flows are smaller than the rated flow of the large device, varying sweep gas $pCO_2$ can predictably change outlet blood $CO_2$ values. This is the testing setup used in Preliminary Studies. The outlet of the large oxygenator is supplied to the servoregulator control system. The controller will then be tested based on its ability to adjust sweep gas flow to achieve a target exhaust gas $CO_2$ level. The servoregulation control system is tested over a range of blood flow 0.5-5 L/min, inlet blood $pCO_2$ 25-100 mmHg, and target exhaust gas $pCO_2$ 5-40 mmHg. Changes in inlet blood $pCO_2$ will simulate patient activity. Inlet and outlet blood gas values are periodically measured throughout the experiment to monitor blood $pCO_2$ and pH. Every 30 min, servoregulation control system sweep flow are decreased to ~100 mL/min, thereby allowing blood $pCO_2$ to equilibrate with exhaust gas $pCO_2$ and thus permitting measurement of blood $PaCO_2$ via the exhaust gas $CO_2$ sensor. $PaCO_2$ measured using the exhaust gas $CO_2$ is compared to blood gas values measured via a blood gas machine. The end point of these experiments is to maintain a desired blood outlet $pCO_2$ over a wide physiologic range of potential use. When the system is optimized we will proceed to animal experiments.

We expect that this aim will result in a fully-functioning compact and light weight servoregulation control system built from commercially-available components and custom electronics. The servoregulation control system will adjust sweep gas flow to achieve the desired exhaust $pCO_2$ in real time (response time <1 min when blood flow or $CO_2$ content is changed). The system will operate over a wide range of air flow, blood flow, air and blood $CO_2$ content, and battery level.

The membrane lung may accumulate water in the gas phase decreasing the $CO_2$ clearance. The servoregulation system should be able to compensate for this by increasing sweep flow. Condensed water in the gas phase may affect the $CO_2$ sensor's performance. A water trap and desiccant have been added before the sensor to remedy this and have been proven effective in preliminary 6 h in vitro tests and 8 h in vivo tests.

This embodiment is deemed successful in that the $CO_2$ servoregulation controller can operate continuously and without failure for 5 days during benchtop testing with water and during 6 h experiments with bovine whole blood. Target $EGCO_2$ is achieved (within 10%) in under 1 minute after any change in blood flow, blood $CO_2$ level, or target $EGCO_2$.

Validation

The acute ovine model described below will provide precise control of animal $PaCO_2$ through control of minute ventilation (MV), and will enable complete testing of the functionality of the $CO_2$ servoregulator control system before proceeding on to chronic testing.

Five healthy adult sheep (60±10 kg; see Vertebrate Animals for justification of animal numbers) were anesthetized following laboratory protocols and maintained with 1-3% inhaled isoflurane as described in the Vertebrate Animals section. For ECMO vascular access, the carotid artery (reinfusion) and the jugular vein (blood drainage) was cannulated with 12-16 Fr cannulas (Bio-Medicus Medtronic, Minneapolis, Minn.) for veno-arterial ECMO. A Swan-Ganz catheter (Edwards Lifesciences, Munich, Germany) was placed in the right internal jugular vein using Seldinger technique. For anticoagulation, a heparin infusion was titrated to maintain an activated clotting (ACT) between 200-250 s. The anesthetized sheep was paralyzed and ventilated. Hypercarbia was induced in the animal by decreasing minute ventilation from 100% baseline to 40% (80 and 40 mL/kg/min, respectively) The animal's arterial $CO_2$ content ($PaCO_2$) was allowed to stabilize with a target between 60 and 80 mmHg. These target $PaCO_2$ values were determined feasible in this animal model in our Preliminary Studies and are clinically-relevant for patients with ESLD. The AL circuit (smart artificial lung and perfusion system 14 and centrifugal pump) and servoregulator system was attached, initially with no sweep gas flow. Extracorporeal blood flow was set to either 1.5 or 3.5 L/min and animal physiology and gas exchange was monitored until it stabilized under two test conditions: 1) Servoregulator off; with the servoregulator off, sweep flow (100% $O_2$) was fixed at a blood:sweep flow ratio of 1:0.5, 1:2, 1:4; and 2) Servoregulator on. With the servoregulator on, target exhaust gas $CO_2$ ($EGCO_2$) was set to 10, 20, and 30 mmHg. The servoregulator was programmed so that it cannot go below a minimum blood:sweep gas flow of 1:0.5 to ensure adequate oxygen delivery to the animal.

All conditions were tested for both animal $PaCO_2$ and hypercapnia conditions. After each test condition, the sweep gas/servoregulator was turned off and animal $PaCO_2$ was allowed to return to baseline (healthy or hypercapnia) before initiating the next test. These experiments will last up to 8 hours. The entire preparation was repeated in 5 sheep to evaluate reproducibility of the results.

The primary endpoints are animal $PaCO_2$ and ECMO function ($CO_2$ and $O_2$ exchange, sweep gas servo controller function, thrombosis). For each 15-min increment, we will record arterial $CO_2$ and AL settings (blood flow/sweep flow) for each minute ventilation scenario (100%, and 50%), with the goal to maintain gas exchange and hemodynamic stability during the duration of the study. Animal $PaCO_2$ and gas exchange at each data point for all five animals was combined into means and standard deviations and compared using Tukey's test. Results were deemed significant for $p<0.05$.

Automated $O_2$ Delivery to Patient

In some embodiments, there is a need to automate the delivery of $O_2$ to patients. Thus, the need for servo regulation of ECMO blood flow to achieve a desired venous oxygen saturation, thereby creating a system that will automatically respond to the changing oxygenation needs of a patient with compromised lung function, was developed.

Although the main need for most ESLD patients is $CO_2$ removal, a subset of patients also requires supplemental blood oxygenation. As with $CO_2$ removal, the patient's need for oxygen varies with metabolism and activity. A large drop in oxygen level risks tissue hypoxia in patients, increasing the probability of multi-organ failure and increasing mortality. For these patients, it would thus be advantageous to control not only $CO_2$ removal but also oxygen delivery via a membrane lung. In AL systems, the amount of oxygenation is primarily controlled by extracorporeal blood flow through the membrane lung, with more flow delivering more oxygen to the patient. In this embodiment, we will thus explore automated control of blood flow and thus oxygen delivery to the patient based on the patient's mixed venous oxygen saturation ($SvO_2$), a direct measure of the patient's oxygen status. Since $SvO_2$ is difficult to measure in veno-venous ECMO due to blood recirculation, this embodiment targets VA ECMO applications. After proof of concept, this work can be applied to VV ECMO by implementing a method to periodically measure blood recirculation. The principles of the present teachings can be leveraged in developing the laptop-based $CO_2$ servoregulation controller to increase the probability of success. This system can first be applied during VA ECMO in the ICU, thereby reducing burden on nurses and doctors for constant monitoring and adjustment of ECMO parameters and increasing patient comfort and safety. Eventually such a system can be implemented in ambulatory and wearable ALs under development.

Figure 8:
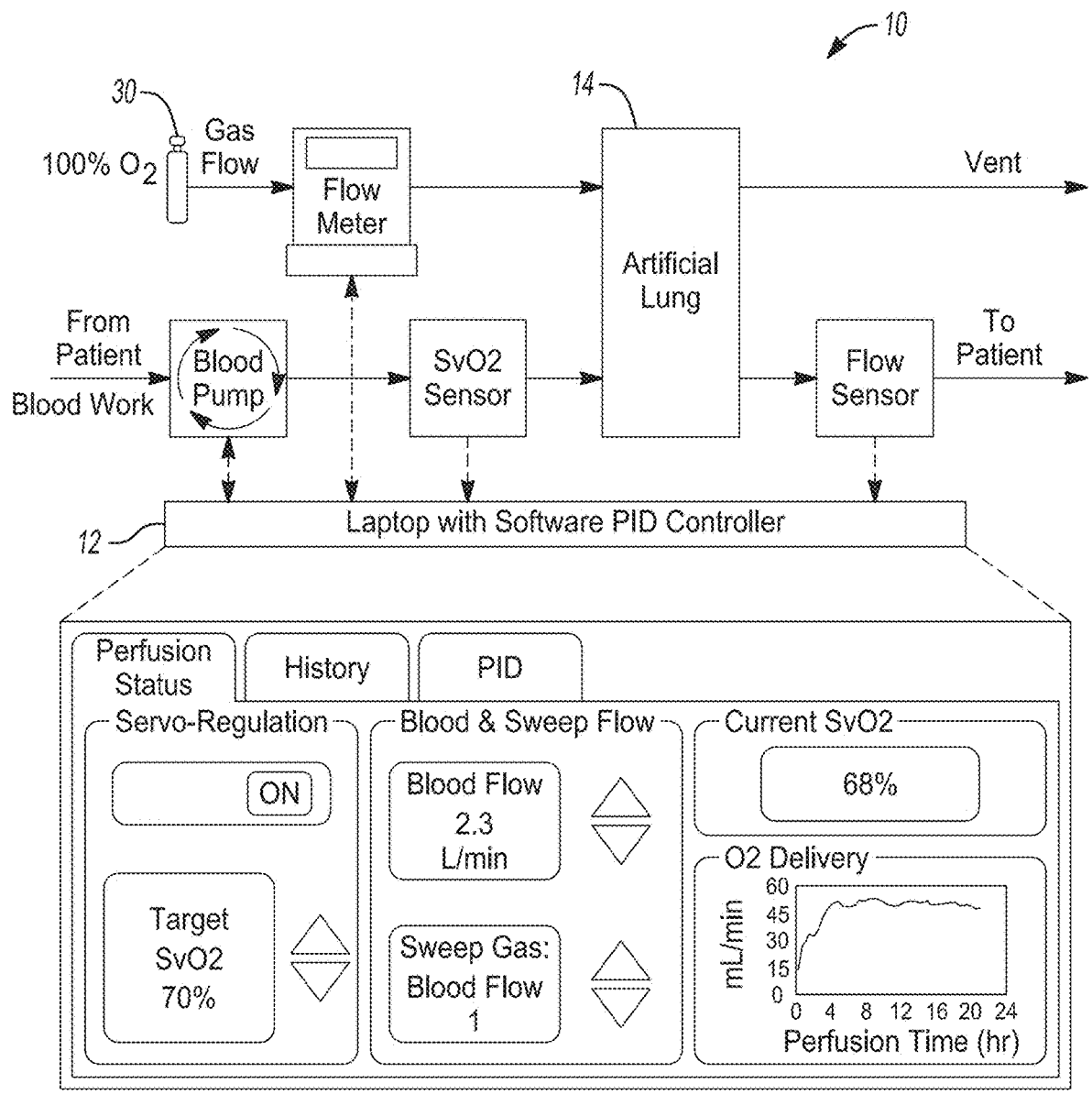
FIG. 8 is a system block diagram for the $SvO_2$-based blood flow servoregulation system and concept drawing of the graphical user interface.
Figure 9:
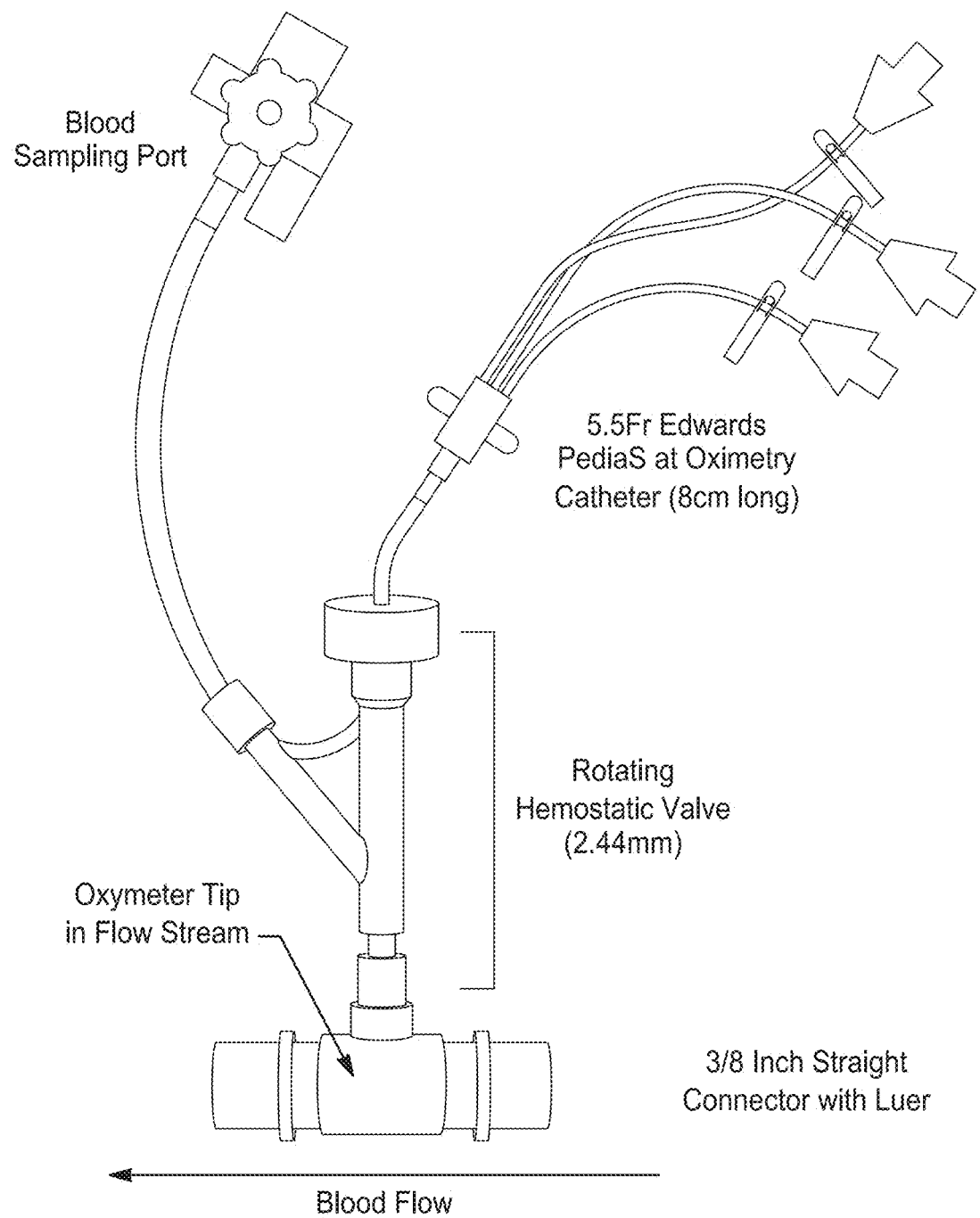
FIG. 9 is the inline $SvO_2$ sensor.

A diagram of the planned $O_2$ delivery servoregulation system is shown in FIG. 8. Laptop-based servoregulator control system 10 was adapted to vary pump-driven blood flow based on $SvO_2$. $SvO_2$ was measured using a modified pediatric oximetry catheter (see FIG. 9) placed in line with the venous tubing. The operation of this modified oximeter was verified during an 8 hour acute sheep study. The user of the $O_2$ servo regulation system (clinical ECMO specialist) will specify a target $SvO_2$ (typically 70%). If measured $SvO_2$ falls below the target $SvO_2$, the controller automatically increases blood flow until the target $SvO_2$ is met. The opposite is true if $SvO_2$ increases, which may occur if patient activity or metabolism decreases or they recover some lung function.

As discussed herein, the user interface and servoregulator controller was programmed on a Microsoft Windows laptop using Microsoft Visual Studio. The $SvO_2$ oximetry sensor was attached to an Edwards Vigilance II Monitor. Communication to the $SvO_2$ sensor will occur via an integrated RS232 serial port on the Vigilance II Monitor. Blood flow was controlled by a Masterflex EW-77921-60 pump with a EW-77253-02 pump head (0-7.6 L/min). Communication will the blood pump will occur via an integrated RS232 serial interface. In preliminary studies, we used a RS232 serial interface to communicate with the $CO_2$ sensor and thus already have this expertise. Blood flow was measured using a Transonic TS410 Blood Flowmeter already available in our laboratory. Sweep gas was controlled via a mass flow controller (Omega FMA-LP1608A, 0-20 L/min) to be a fixed ratio (set by the user) relative to the current blood flow. The user will also be able to set maximum and minimum sweep and blood flows.

Testing of all individual components and the integrated system will initially be accomplished with our bench system and water flow. The system was perfused with water at room temperature continuously for 5 days. The sweep gas was 5% $CO_2$ in air, allowing evaluation of the $SvO_2$ sensor under continuous use and clinically relevant $pO_2$ and $pCO_2$ values. This bench testing will verify the operation and reliability of the control software, sensors, and user interface. After verification of the durability of components, bench testing will proceed with fresh bovine blood. The bench test system includes a blood reservoir that mimics a patient's blood volume. The patient's gas exchange and metabolism ($O_2$ consumption) are mimicked by a large oxygenator (Quadrox D) through which blood is pumped through then delivered back to the reservoir. Changing either blood or sweep flow to the large oxygenator can predictably change oxygen removal, thereby mimicking changes in a patient's oxygen consumption and $SvO_2$. After a baseline $SvO_2$ and oxygen consumption rate are determined, the servoregulator system was turned on. The servoregulation system (and corresponding oxygenator) is in parallel with the large oxygenator (that mimics patient $O_2$ consumption). The servoregulation system reads the incoming $SvO_2$ from the blood reservoir and attempts to modify blood flow (and thus oxygen delivery) to the reservoir (patient) in order to meet a desired $SvO_2$. This is a slightly modified version of the testing setup from Preliminary Studies. The servoregulation controller was tested based on its ability to adjust blood flow to achieve a target reservoir $SO_2$ level (simulates $SvO_2$). The servoregulation control system was tested over a range of blood flow to sweep flow ratios, inlet blood $O_2$ 25-70 mmHg, target $SvO_2$, and "patient" oxygen consumption rates. AL inlet and outlet blood gas values was periodically measured throughout the experiment to monitor blood $pO_2$ and $SO_2$. The end point of these experiments was to maintain a desired blood $SvO_2$ over a wide physiologic range of potential use. Servoregulation was compared to the same experiment, but with blood flow held constant at either 1 or 4 L/min (1:1 sweep flow).

The bench studies was repeated in triplicate. Measurements were converted to means and standard deviations. Results from servoregulation were compared to constant blood flow condition using Tukey's test. Results were deemed significant for $p<0.05$.

The present embodiments result in a fully functioning AL system capable of automatically adjusting oxygen delivery (blood flow) based on patient metabolic status ($SvO_2$). The servoregulation control system 10 adjusts blood flow to achieve the desired $SvO_2$. Because the effects of servoregulation are systemic (via affecting $SvO_2$ in the reservoir), the response time of the present system is likely to be slower than in the sweep gas servoregulator. We expect that the system will operate over a wide range of blood flow, target $SvO_2$, and inlet blood $SO_2$ values.

This embodiment results in a servoregulation system that can adjust oxygen delivery (blood flow) to a patient based on a target $SvO_2$ level. Reservoir $SO_2$ ($SvO_2$) should stabilize to the target value within 15 minutes.

Overall, the present teachings result in the first artificial lung controllers capable of rapidly and automatically responding to the changing $CO_2$ removal and oxygenation needs of ESLD patients. The sweep gas ($CO_2$) servoregulation controller is ready for extended large animal testing, integration into specific artificial lungs systems, and for an FDA IDE. The blood flow ($O_2$) servoregulator is ready for integration into the compact sweep gas controller and for animal testing. These technologies will form the basis of a new class of smart artificial lung/ECMO controllers that require minimal user intervention, improve patient health and comfort, and, after integration into wearable artificial lung systems, enable ESLD patients to potentially return home.

According to these principles, some embodiments of the present teachings provide an artificial lung system for a patient having a membrane lung system having an gas inlet, a blood inlet, a blood outlet, and an exhaust; an air pump operably coupled to the gas inlet of the membrane lung system for introducing air to the membrane lung system; a gas phase $CO_2$ sensor disposed downstream of the exhaust of the membrane lung system and monitoring an exhaust gas $CO_2$ ($EGCO_2$) level, the gas phase $CO_2$ sensor outputting a $CO_2$ signal in response to a detected $EGCO_2$ level; and a proportional-integral-derivative (PID) feedback controller receiving the $CO_2$ signal and outputting an air pump control signal to the air pump responsive thereto such that if $EGCO_2$ content increases relative to a target $CO_2$ level, the feedback controller increases sweep flow of the air pump to remove more $CO_2$ from the blood flowing through the blood inlet to the blood outlet, if $EGCO_2$ content decreases relative to the target $CO_2$ level, the feedback controller automatically decreases sweep flow of the air pump to reduce $CO_2$ removal.

In some embodiments, this artificial lung system can further include a water trap being disposed between the exhaust of the membrane lung system and the gas phase $CO_2$ sensor.

In some embodiments, this artificial lung system can further include an oximeter disposed upstream from the inlet of the membrane lung system.

In some embodiments, this artificial lung system can further include an $SvO_2$ sensor disposed upstream of the blood inlet of the membrane lung system and monitoring an $SvO_2$ level, the $SvO_2$ sensor outputting a $SvO_2$ signal in response to a detected $SvO_2$ level, wherein the proportional-integral-derivative (PID) feedback controller receiving the $SvO_2$ signal and outputting a blood flow control signal to control the flow of blood through the membrane lung system. It should be noted that the teachings of the present invention are not limited to venous oxygen ($SvO_2$) and, thus, any embodiment monitoring blood oxygen saturation ($SO_2$) with associated sensors is within the scope of the present teachings. Moreover, these teachings are applicable to monitoring other blood qualities, such as partial pressure ($PO_2$), can be used with associated sensors.

According to these principles, some embodiments of the present teachings provide an artificial lung system for a patient having a membrane lung system having an gas inlet, a blood inlet, a blood outlet, and an exhaust; a gas system operably coupled to the gas inlet of the membrane lung system for introducing gas to the membrane lung system; a gas phase $CO_2$ sensor disposed downstream of the exhaust of the membrane lung system and monitoring an exhaust gas $CO_2$ ($EGCO_2$) level, the gas phase $CO_2$ sensor outputting a $CO_2$ signal in response to a detected $EGCO_2$ level; and a proportional-integral-derivative (PID) feedback controller receiving the $CO_2$ signal and outputting an gas system control signal to the gas system responsive thereto such that if $EGCO_2$ content increases relative to a target $CO_2$ level, the feedback controller increases sweep flow of the gas system to remove more $CO_2$ from the blood flowing through the blood inlet to the blood outlet, if $EGCO_2$ content decreases relative to the target $CO_2$ level, the feedback controller automatically decreases sweep flow of the gas system to reduce $CO_2$ removal.

In some embodiments, this artificial lung system can further include a water trap being disposed between the exhaust of the membrane lung system and the gas phase $CO_2$ sensor.

In some embodiments, this artificial lung system can further include an oximeter disposed upstream from the inlet of the membrane lung system.

In some embodiments, the gas system includes a gas cylinder.

In some embodiments, the gas system comprises an oxygen concentrator.

In some embodiments, the gas system comprises a gas flow controller.

In some embodiments, this artificial lung system can further include an $SvO_2$ sensor disposed upstream of the blood inlet of the membrane lung system and monitoring an $SvO_2$ level, the $SvO_2$ sensor outputting a $SvO_2$ signal in response to a detected $SvO_2$ level, wherein the proportional-integral-derivative (PID) feedback controller receiving the $SvO_2$ signal and outputting a blood flow control signal to control the flow of blood through the membrane lung system.

According to these principles, some embodiments of the present teachings provide a membrane lung system having an gas inlet, a blood inlet, a blood outlet, and an exhaust; a gas system operably coupled to the gas inlet of the membrane lung system for introducing gas to the membrane lung system; an $SvO_2$ sensor disposed upstream of the blood inlet of the membrane lung system and monitoring an $SvO_2$ level, the $SvO_2$ sensor outputting a $SvO_2$ signal in response to a detected $SvO_2$ level; and a proportional-integral-derivative (PID) feedback controller receiving the $SvO_2$ signal and outputting a blood flow control signal to control the flow of blood through the membrane lung system.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An artificial lung system for a patient, the system comprising:
    a membrane lung system having an gas inlet, a blood inlet, a blood outlet, and an exhaust;
    a gas system operably coupled to the gas inlet of the membrane lung system for introducing gas to the membrane lung system;
    a gas phase CO2 sensor disposed downstream of the exhaust of the membrane lung system and monitoring an exhaust gas CO2 (EGCO2) level, the gas phase CO2 sensor outputting a CO2 signal in response to a detected EGCO2 level; and
    a feedback controller receiving the CO2 signal and outputting an gas system control signal to the gas system responsive thereto such that if EGCO2 content increases relative to a target CO2 level, the feedback controller increases sweep flow of the gas system to remove more CO2 from the blood flowing through the blood inlet to the blood outlet, if EGCO2 content decreases relative to the target CO2 level, the feedback controller automatically decreases sweep flow of the gas system to reduce CO2 removal.

2. The artificial lung system according to claim 1, further comprising:
    a water trap being disposed between the exhaust of the membrane lung system and the gas phase CO2 sensor.

3. The artificial lung system according to claim 1, further comprising:
    a blood oximeter disposed upstream from the blood inlet of the membrane lung system.

4. The artificial lung system according to claim 1 wherein the gas system comprises a gas cylinder.

5. The artificial lung system according to claim 1 wherein the gas system comprises an oxygen concentrator.

6. The artificial lung system according to claim 1 wherein the gas system comprises a gas flow controller.

7. The artificial lung system according to claim 1, further comprising:
    a blood oxygen saturation sensor disposed upstream of the blood inlet of the membrane lung system and monitoring a blood oxygen saturation level, the blood oxygen saturation sensor outputting a blood oxygen saturation signal in response to a detected blood oxygen saturation level,
    wherein the feedback controller receiving the blood oxygen saturation signal and outputting a blood flow control signal to control the flow of blood through the membrane lung system.

8. The artificial lung system according to claim 1 wherein the feedback controller comprises a proportional-integral-derivative (PIO) feedback controller.

* * * * *